(12) United States Patent
Chang

(10) Patent No.: US 8,176,919 B2
(45) Date of Patent: May 15, 2012

(54) RESPIRATORY MASK INCLUDING AN ADJUSTABLE FOREHEAD ABUTMENT MEMBER

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 378 days.

(21) Appl. No.: 12/607,763

(22) Filed: Oct. 28, 2009

(65) Prior Publication Data

US 2011/0094516 A1   Apr. 28, 2011

(51) Int. Cl.
*A62B 18/08* (2006.01)
(52) U.S. Cl. ......... 128/206.28; 128/207.11; 128/206.21; 128/206.24
(58) Field of Classification Search ............ 128/205.25, 128/206.21, 206.24, 206.27, 207.13, 205.27, 128/207.11, 206.28
See application file for complete search history.

(56) References Cited

U.S. PATENT DOCUMENTS

| | | | |
|---|---|---|---|
| 7,047,971 B2* | 5/2006 | Ho et al. ................... | 128/207.11 |
| 7,610,916 B2* | 11/2009 | Kwok et al. ............. | 128/207.11 |
| 2008/0135050 A1* | 6/2008 | Hitchcock et al. ........ | 128/207.11 |
| 2008/0314390 A1* | 12/2008 | Kwok et al. ............. | 128/207.11 |

* cited by examiner

*Primary Examiner* — Steven Douglas
(74) *Attorney, Agent, or Firm* — Occhiuti Rohlicek & Tsao LLP

(57) ABSTRACT

An adjustable respiratory mask includes: a mask body including a rear side, and a front cover having a connecting hole and projecting upwardly; an adjuster housing formed on top of the front cover, and having a sleeve that extends within the adjuster housing in a front-to-rear direction and that has a rear opening exposed from the adjuster housing; a forehead abutment member having a shank projecting forwardly from the forehead abutment member and extending into the sleeve through the rear opening; and an adjusting unit for adjusting a distance of the forehead abutment member from the adjuster housing. The shank is movable relative to the sleeve so that the forehead abutment member is movable toward and away from the adjuster housing.

6 Claims, 9 Drawing Sheets

RESPIRATORY MASK INCLUDING AN ADJUSTABLE FOREHEAD ABUTMENT MEMBER

BACKGROUND OF THE INVENTION

1. Field of the Invention

This invention relates to a respiratory mask, more particularly to a respiratory mask including an adjustable forehead abutment member.

2. Description of the Related Art

A conventional respiratory mask includes a mask body adapted to cover a user's nose and/or mouth, a cover shell connected to the mask body and having a gas inlet hole, and a support unit extending from the cover shell toward the forehead of the user.

In use, the user's nose and/or mouth are covered by the mask body, and the gas inlet hole is connected to a pump through an air supply tube. When the pump is operated to produce a continuous positive pressure airflow into the mask through the gas inlet hole, the user can smoothly breathe by virtue of the airflow. Since the user usually wears the respiratory mask for a long period of time and may feel uncomfortable due to weight of the respiratory mask continuously forced thereon, the support unit is provided to alleviate the discomfort.

However, the support unit having an invariable size is not suited for accommodating of a variety of facial differences among individuals.

SUMMARY OF THE INVENTION

Therefore, an object of the present invention is to provide a respiratory mask that can overcome the aforesaid drawback associated with the prior art.

According to the present invention, an adjustable respiratory mask comprises: a mask body including a rear side adapted to contact a user's nose and/or mouth, and a front cover having a connecting hole and projecting upwardly; an adjuster housing formed on top of the front cover, and having a sleeve that extends within the adjuster housing in a front-to-rear direction and that has a rear opening exposed from the adjuster housing; a forehead abutment member adapted to abut against a forehead of the user, and having a shank projecting forwardly from the forehead abutment member and extending into the sleeve through the rear opening, the shank being movable relative to the sleeve so that the forehead abutment member is movable toward and away from the adjuster housing; and an adjusting unit for adjusting a distance of the forehead abutment member from the adjuster housing.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
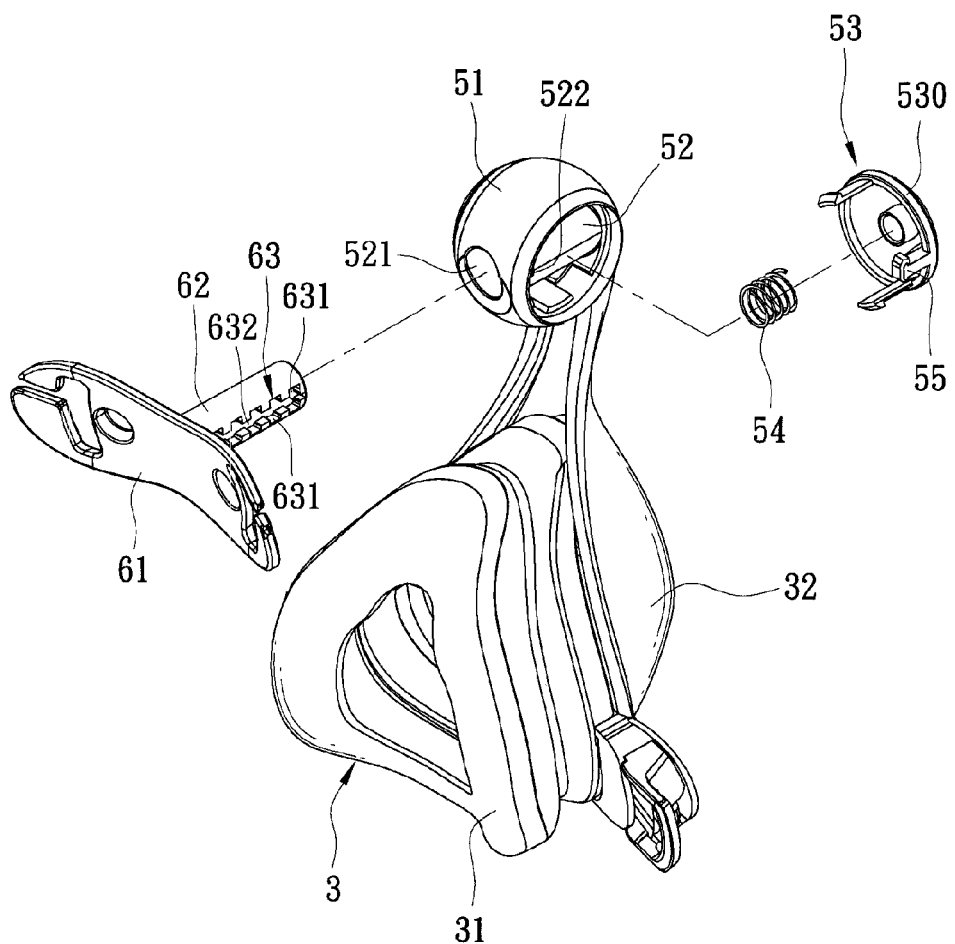
FIG. 1 is an exploded perspective view of a preferred embodiment of an adjustable respiratory mask according to this invention.
Figure 2:
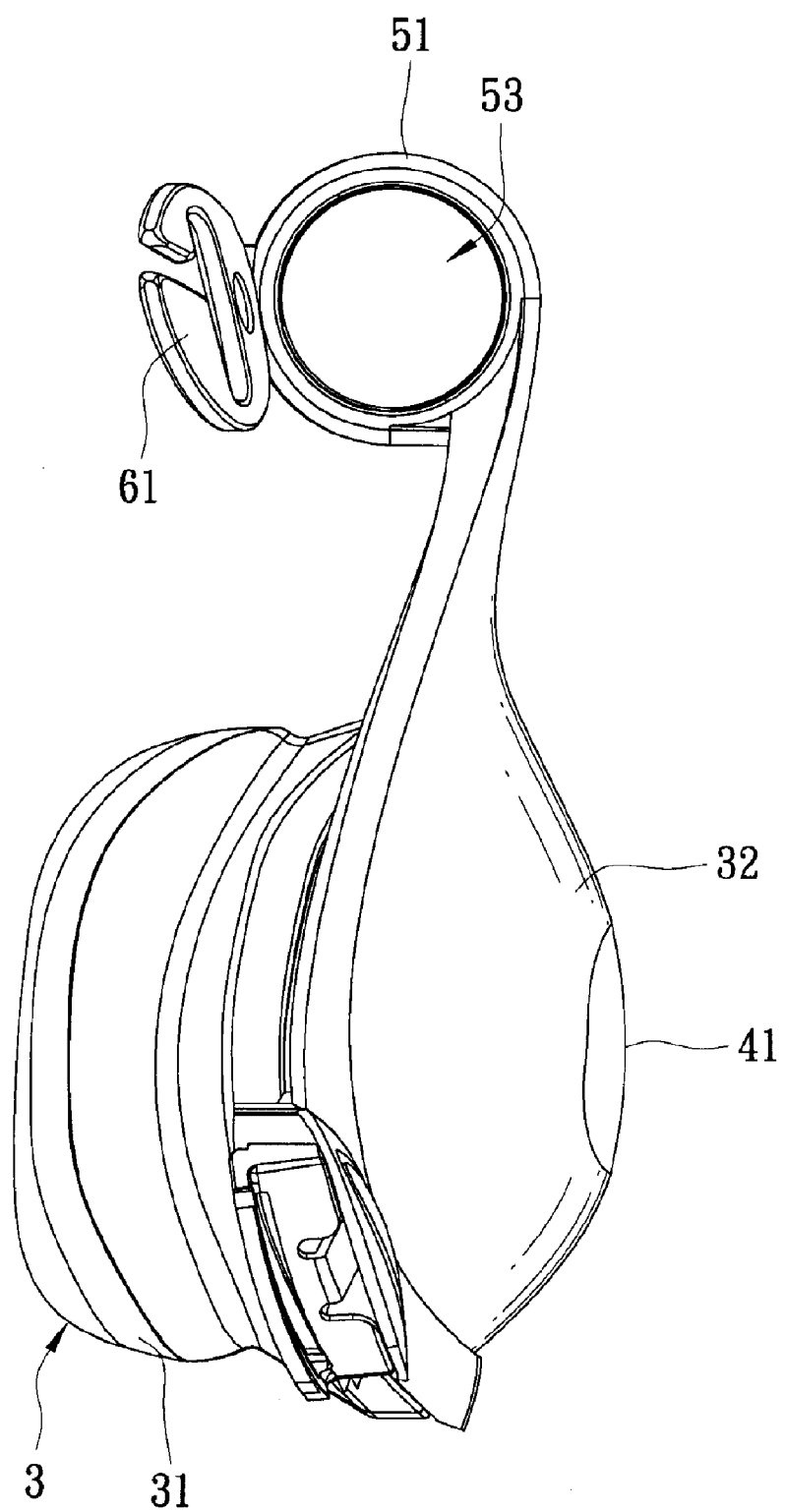
FIG. 2 is an assembled perspective view of the preferred embodiment.

Referring to FIGS. 1 and 2, an adjustable respiratory mask 2 of a preferred embodiment according to this invention includes a mask body 3, an adjuster housing 51, a forehead abutment member 61, and an adjusting unit.

The mask body 3 includes a rear side 31 adapted to contact a user's nose and/or mouth, and a front cover 32 opposite to the rear side 31, projecting upwardly and formed with a connecting hole 41.

Figure 3:
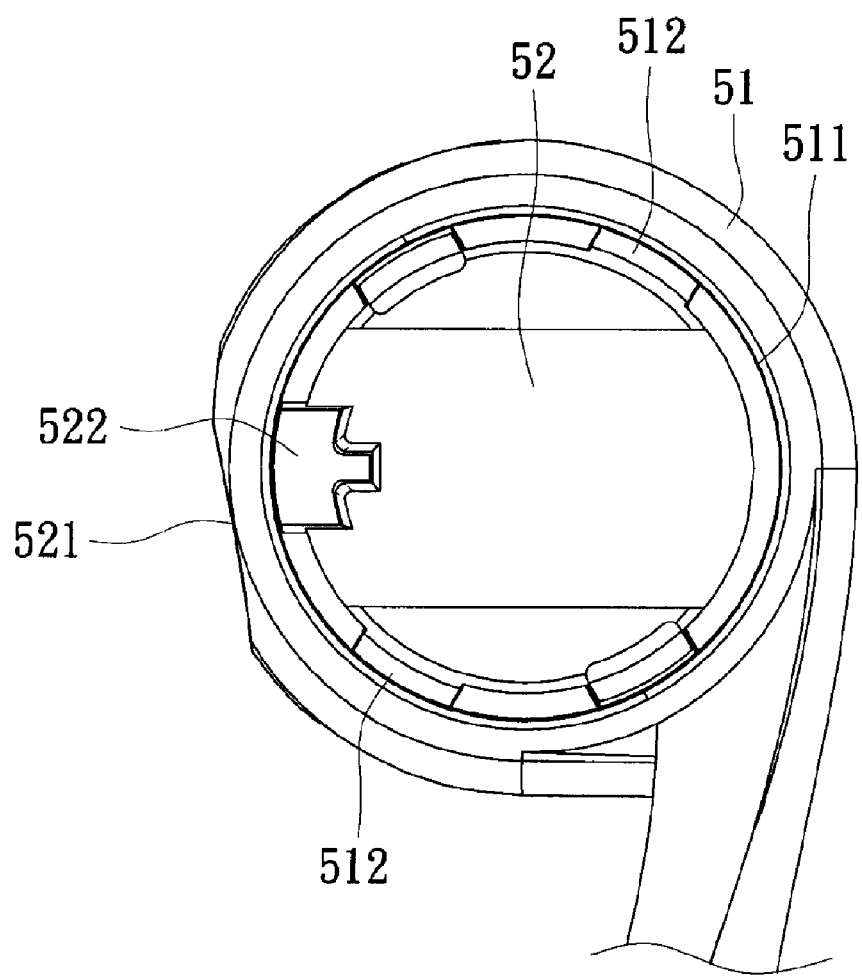
FIG. 3 is a fragmentary side view of an adjuster housing of the preferred embodiment.
Figure 4:
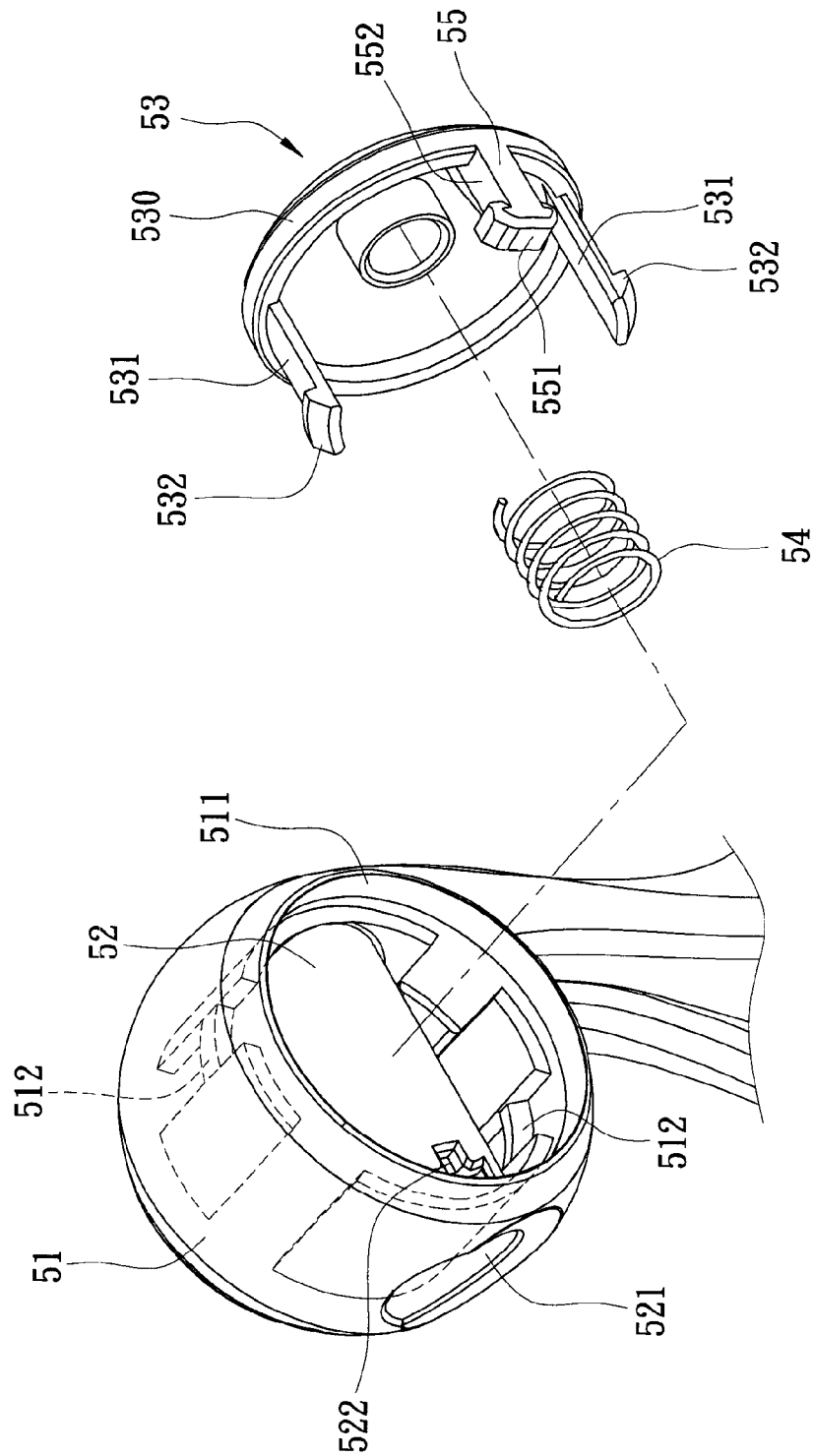
FIG. 4 is a fragmentary exploded perspective view of the preferred embodiment.

Referring to FIGS. 1, 3 and 4, the adjuster housing 51 is formed on top of the front cover 32 and has a sleeve 52 that extends within the adjuster housing 51 in a front-to-rear direction and that has a rear opening 521 exposed from the adjuster housing 51. The sleeve 52 has a through passage 522 spatially communicating with the rear opening 521.

The forehead abutment member 61 is adapted to abut against a forehead of the user, and has a shank 62 projecting forwardly from the forehead abutment member 61 and extending movably into the sleeve 52 through the rear opening 521.

The adjusting unit has an actuating member 53 attached to one side of the adjuster housing 51 and operable to move transversely of the sleeve 52. The actuating member 53 has a disk 530 and a resilient member 54 disposed between the sleeve 52 and the disk 530. In this embodiment, the resilient member 54 is a spring.

The adjuster housing 51 further has a side hole 511 for receiving the disk 530 therein, and an inner wall surface formed with a pair of engagement ribs 512.

The actuating member 53 further has two parallel resilient arms 531 protruding from the disk 530 and formed respectively with hook ends 532. The hook ends 532 are respectively engaged with the engagement ribs 512.

The adjusting unit further includes an adjustment groove 63 extending axially in a tubular wall of the shank 62, and a locking member 55 disposed in the adjuster housing 51 and extendable into the sleeve 52 through the through passage 522 to engage the adjustment groove 63.

The locking member 55 has a stem portion 552 connected to the disk 530 of the actuating member 53 and a butt end 551 formed at one end of the stem portion 552 opposite to the disk 530. The adjustment groove 63 includes five locking groove portions 631 which are spaced apart axially from each other and which extend circumferentially, and a slide groove portion 632 axially extending and intersecting the locking groove portions 631. The butt end 551 is engageable with one of the locking groove portions 631. The width of the slide groove portion 632 is smaller than that of the butt end 551. The stem portion 552 is slidable along the slide groove portion 632 to permit the butt end 551 to move between the locking groove portions 631.

In assembly, the shank 62 extends into the sleeve 52 through the rear opening 521, and the actuating member 53 is fitted in the side hole 511 of the adjuster housing 51 such that the locking member 55 extends into the sleeve 52 through the through passage 522.

Figure 5:
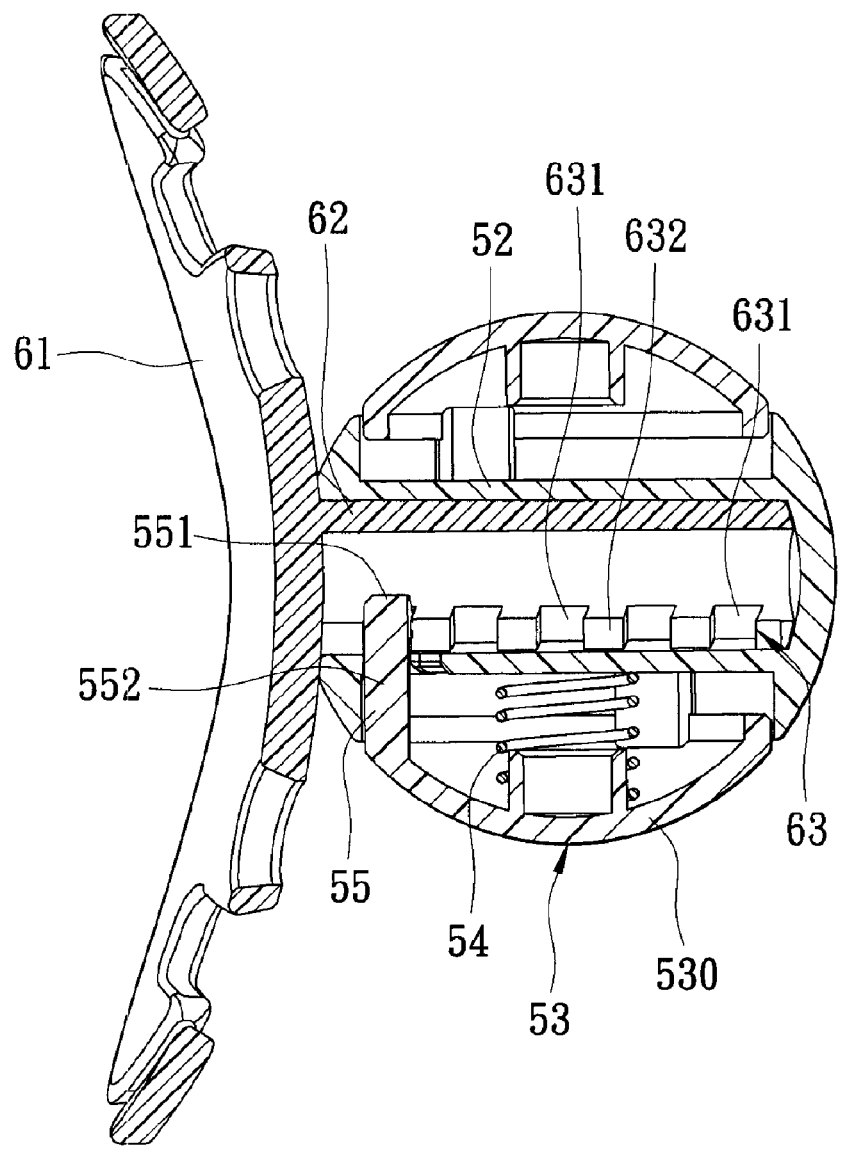
FIG. 5 is a fragmentary sectional view illustrating a locking member engaging an adjusting groove within the adjuster housing.
Figure 6:
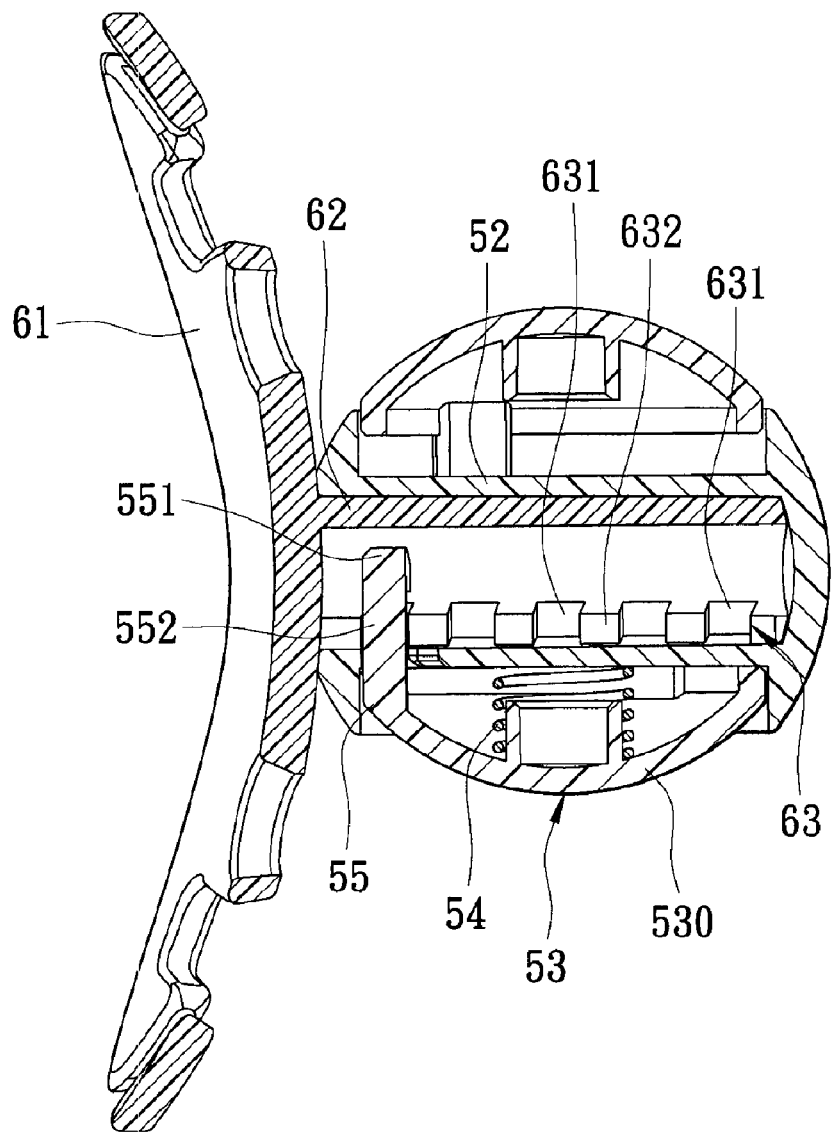
FIG. 6 is the same view as FIG. 5, but illustrating the locking member disengaged from the adjusting groove.
Figure 7:
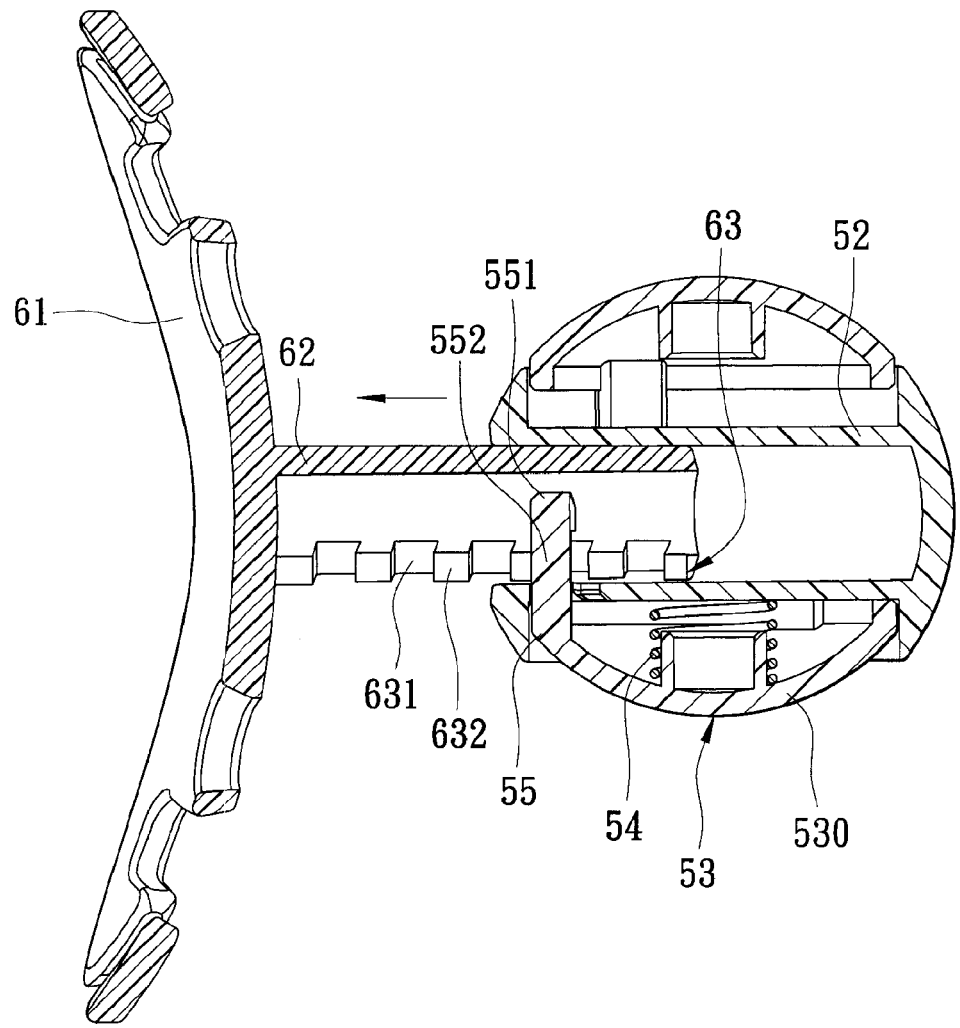
FIG. 7 is the same view as FIG. 5, but illustrating a forehead abutment member moved rearward from the adjuster housing.

Referring to FIGS. 5, 6, and 7, the shank 62 is movable relative to the sleeve 52 so that the forehead abutment member 61 is movable toward and away from the adjuster housing 51. The locking member 55 is movable between a locking position and a non-locking position. Referring back to FIG. 5, at the locking position, the resilient member 54 urges the disk 530 to move outwardly so that the butt end 551 of the locking member 55 engages one of the locking groove portions 631, thereby locking the forehead abutment member 61 against movement. Referring back to FIG. 6, when the distance of the forehead abutment member 61 is to be adjusted, the disk 530 of the actuating member 53 is pressed inwardly by a force such that the locking member 55 is moved inwardly into the sleeve 52, and such that the butt end 551 of the locking member 55 is disengaged from the locking groove portion 631 that is originally in engagement therewith. When the shank 62 is moved along the front-to-rear direction, the stem portion 552 is slid along the slide groove portion 632, thereby adjusting the distance of the forehead abutment member 61 from the adjuster housing 51, as shown in FIG. 7.

When the force applied on the disk 530 is removed, the resilient member 54 urges the disk 530 to move outwardly so that the butt end 551 of the locking member 55 engages another of the locking groove portions 631, thereby once again locking the forehead abutment member 61 and the shank 62 against movement.

Figure 8:
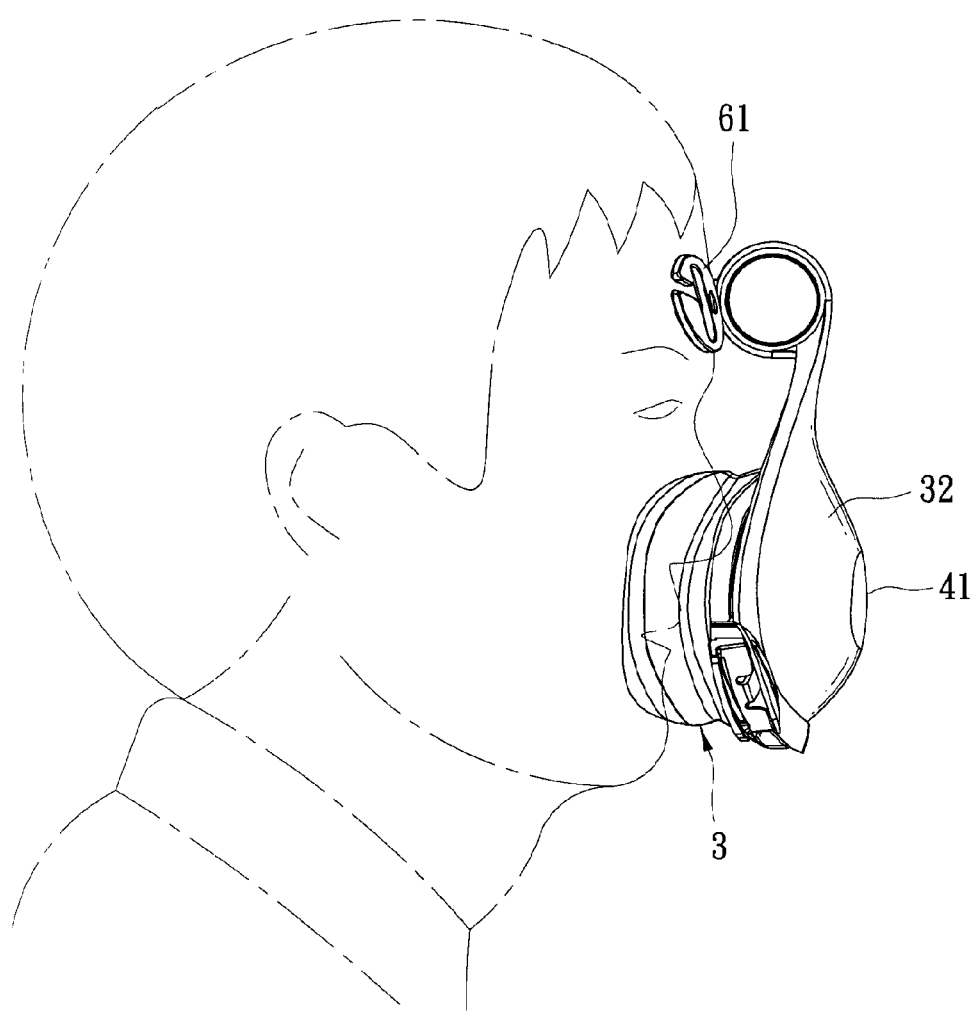
FIG. 8 is a perspective view of the preferred embodiment showing that the respiratory mask is used to cover a user's nose and mouth.
Figure 9:
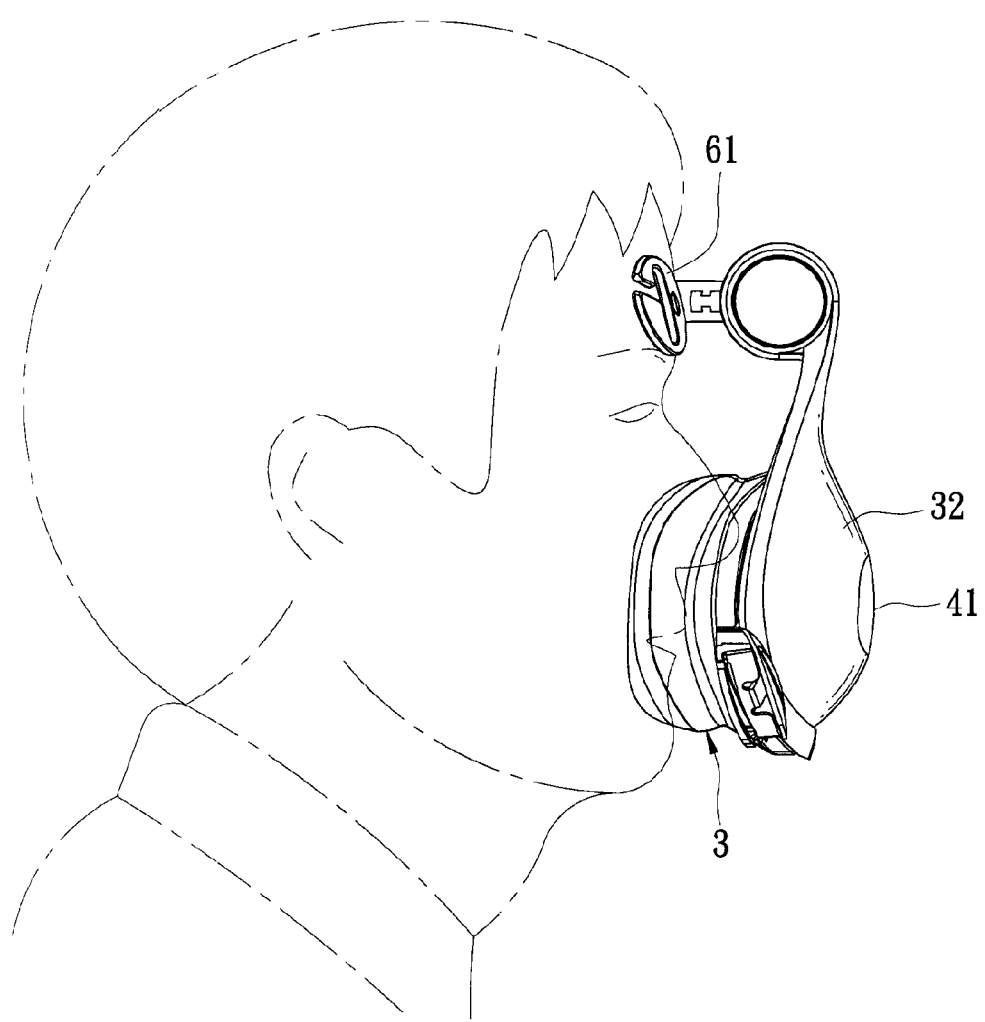
FIG. 9 is the same view as FIG. 8, but illustrating the forehead abutment member after adjustment.

Referring to FIGS. 8 and 9, a pump (not shown) is operated to produce a continuous positive pressure airflow into the mask through an air supply tube (not shown) and the connecting hole 41, which is beneficial for a patient to smoothly breathe. By virtue of the adjusting unit, a position of the forehead abutment member 61 relative to the mask body 3 can be adjusted so as to alleviate an overpress on the user's nose, whereby the user can feel more comfortable.

With the invention thus explained, it is apparent that various modifications and variations can be made without departing from the spirit of the present invention. It is therefore intended that the invention be limited only as recited in the appended claims.

What is claimed is:

1. An adjustable respiratory mask comprising:
    a mask body including a rear side adapted to contact a user's nose and/or mouth, and a front cover having a connecting hole and projecting upwardly;
    an adjuster housing formed on top of said front cover, and having a sleeve that extends within said adjuster housing in a front-to-rear direction and that has a rear opening exposed from said adjuster housing;
    a forehead abutment member adapted to abut against a forehead of the user, and having a shank projecting forwardly from said forehead abutment member and extending into said sleeve through said rear opening, said shank being movable relative to said sleeve so that said forehead abutment member is movable toward and away from said adjuster housing; and
    an adjusting unit for adjusting a distance of said forehead abutment member from said adjuster housing.

2. The respiratory mask of claim 1, wherein said shank has a tubular wall, said adjusting unit including an adjustment groove extending axially in said tubular wall, and a locking member disposed in said adjuster housing and extendable into said sleeve to engage said adjustment groove.

3. The respiratory mask of claim 2, wherein said sleeve has a through passage, said adjusting unit further having an actuating member attached to one side of said adjuster housing and operable to move transversely of said sleeve, said locking member being connected to said actuating member and extending into said sleeve through said through passage, said locking member being moved to engage or disengage said adjustment groove when said actuating member is operated.

4. The respiratory mask of claim 3, wherein said adjuster housing further has a side hole, said actuating member having a disk fitted movably in said side hole, and a resilient member disposed between said sleeve and said disk to urge said disk to move outwardly so that said locking member engages said adjustment groove, said locking member being disengaged from said adjustment groove when said disk is pressed inwardly.

5. The respiratory mask of claim 4, wherein said locking member has a stem portion connected to said disk, and a butt end connected to one end of said stem portion opposite to said disk, said adjustment groove including a plurality of locking groove portions which are spaced apart axially from each other and which extend circumferentially, and a slide groove portion axially extending and intersecting said locking groove portions, said butt end being engageable with one of said locking groove portions, said stem portion being slidable along said slide groove portion to permit said butt end to move between said locking groove portions.

6. The respiratory mask of claim 4, wherein said actuating member further has two resilient arms protruding inwardly from said disk, and formed respectively with hook ends, and said adjuster housing further has an inner wall surface formed with a pair of engagement ribs to engage said hook ends, respectively.

* * * * *